United States Patent
Biel et al.

(10) Patent No.: US 8,318,968 B2
(45) Date of Patent: Nov. 27, 2012

(54) PROCESS FOR PREPARING AN ALKENYLPHOSPHONIC ACID DERIVATIVE

(75) Inventors: Markus Christian Biel, Mannheim (DE); Roland Kessinger, Weinheim (DE); Jens Sommer, Unna (DE); Janet Bluemel, College Station, TX (US)

(73) Assignee: BASF SE, Ludwigshafen (DE)

( * ) Notice: Subject to any disclaimer, the term of this patent is extended or adjusted under 35 U.S.C. 154(b) by 477 days.

(21) Appl. No.: 12/530,838

(22) PCT Filed: Mar. 17, 2008

(86) PCT No.: PCT/EP2008/053143
§ 371 (c)(1),
(2), (4) Date: Sep. 11, 2009

(87) PCT Pub. No.: WO2008/113777
PCT Pub. Date: Sep. 25, 2008

(65) Prior Publication Data
US 2010/0121092 A1    May 13, 2010

(30) Foreign Application Priority Data
Mar. 22, 2007  (EP) .................................... 07104651

(51) Int. Cl.
C07F 9/40         (2006.01)
(52) U.S. Cl. ....................................................... 558/137
(58) Field of Classification Search ................... 558/137
See application file for complete search history.

(56) References Cited

U.S. PATENT DOCUMENTS 3,093,672 A * 6/1963 Miller ........................... 558/160
3,673,285 A    6/1972 Lin
6,534,669 B2   3/2003 Klass et al.
7,399,876 B2 * 7/2008 Kessinger et al. ............ 558/137
2003/0166612 A1  9/2003 Han et al.
2005/0113593 A1 * 5/2005 Kessinger et al. ............ 558/109
2005/0113602 A1 * 5/2005 Kessinger et al. ................ 562/8

FOREIGN PATENT DOCUMENTS

| EP | 1 203 773 | 5/2002 |
| EP | 1 528 064 | 5/2005 |
| EP | 1 528 065 | 5/2005 |

OTHER PUBLICATIONS

Kaljurand et al. "Extension of the Self-Consistent Spectrophotometric Basicity Scale in Acetonitrile to a Full Span of 28 pKa Units: ‰ Unification of Different Basicity Scales" Journal of Organic Chemistry, 2005, vol. 70, pp. 1019-1028.*
Han et al. "Efficient and Selective Nickel-Catalyzed Addition of H-P(O) and H-S Bonds to Alkynes" Journal of the American Chemical Society, 2004, vol. 126, pp. 5080-5081.*
Han, L.-B. et al., "Nickel-Catalyzed Addition of P(O)-H Bonds to Propargyl Alcohols: One-Pot Generation of Phosphinoyl 1,3-Butadienes", Organic Letters, vol. 7, No. 14, pp. 2909-2911 (2005) XP-002476434.
Han, L.-B. et al., "Palladium-Catalyzed Hydrophosphorylation of Alkynes Via Oxidative Addition of HP(O)(OR)$_2$", Journal of the American Chemical Society, vol. 118, No. 6, pp. 1571-1572 (1996) XP-002476435.
Han, L.-B. et al., "Efficient and Selective Nickel-Catalyzed Addition of H-P(O) and H-S Bonds to Alkynes", Journal of the American Chemical Society, vol. 126, No. 16, pp. 5080-5081 (2004) XP-002476436.

* cited by examiner

*Primary Examiner* — Joseph Kosack
(74) *Attorney, Agent, or Firm* — Oblon, Spivak, McClelland, Maier & Neustadt, L.L.P.

(57) ABSTRACT

Process for preparing an alkenylphosphonic acid derivative by reacting a phosphonic acid derivative with an alkyne in the presence of a complex catalyst system and a base whose conjugate acid has a pKa in dimethyl sulfoxide (25° C., 1 bar) of at least 6.

16 Claims, No Drawings

PROCESS FOR PREPARING AN ALKENYLPHOSPHONIC ACID DERIVATIVE

The present invention relates to a process for preparing an alkenylphosphonic acid derivative by reacting a phosphonic acid derivative with an alkyne in the presence of a complex catalyst system.

Vinylphosphonic acid derivatives, in particular dialkyl vinylphosphonates, are important as intermediates for the preparation of vinylphosphonic acids and as monomers for copolymerization for the production of adhesives and flame-resistant plastics.

Various processes for preparing them are known.

One process for preparing alkenylphosphonic diesters is the addition of alkynes onto phosphonic diesters in the presence of a palladium complex catalyst. An advantage of this synthetic route is a pure addition reaction without formation of stoichiometric amounts of by-products or coproducts. A disadvantage is the use of the expensive noble metal catalyst.

U.S. Pat. No. 3,673,285 describes the addition of alkynes onto phosphonic diesters to form alkenylphosphonic diesters at temperatures of from 130 to 200° C. in the presence of nickel complex catalysts from the group consisting of dicarbonylbis(triphenylphosphino)nickel(0), bis(tris(hydroxymethyl)phosphino)nickel(II) chloride, bis(tri-n-butylphosphino)nickel(II) bromide and tetracarbonylnickel(0). In the case of the addition of ethyne onto diethyl phosphite, a yield of diethyl vinylphosphonate of 40% was achieved in the presence of bis(tri-n-butylphosphino)nickel(II) bromide (Example 15). Disadvantages of this process are a low yield of significantly below 50% and the necessity of a high reaction temperature of up to 200° C., which leads to exothermic decomposition of the ethyl phosphonate.

EP-A1-1 203 773 (BASF Aktiengesellschaft) describes a process for preparing alkenylphosphonic acid derivatives by reacting phosphonic acid derivatives with alkynes in the presence of a complex catalyst system comprising (a) nickel and (b) a phosphine having at least two trivalent phosphorus atoms.

EP-A-1 528 064 describes a process for preparing an alkenylphosphonic acid derivative by reacting a phosphonic acid derivative with an alkyne in the presence of a complex catalyst system, which is characterized in that the complex catalyst system comprises (a) nickel, (b) a phosphine having at least two trivalent phosphorus atoms and (c) a phosphine having one trivalent phosphorus atom.

EP-A-1 528 065 (BASF Aktiengesellschaft) describes a corresponding process in which the alkyne is added only after the phosphonic acid derivative has been brought into contact with the complex catalyst system for at least one minute.

These processes result in an improvement in the yield and selectivity. However, a further improvement in the yield and selectivity is still possible and desirable. Further improvements may be able to be achieved if the industrial phosphonic acid derivatives used in the reaction are purified beforehand, e.g. by distillation, and by-products, e.g. acids, are separated off.

It was an object of the invention to find a process for preparing alkenylphosphonic acid derivatives which overcomes the disadvantages of the prior art, does not form any coproducts, permits a reaction temperature of significantly below 200° C., makes a high yield of significantly above 50%, in particular above 75%, possible and makes do without the use of an expensive noble metal catalyst and also without prior purification or distillation of the phosphonic acid derivatives.

We have accordingly found a process for preparing an alkenylphosphonic acid derivative by reacting a phosphonic acid derivative with an alkyne in the presence of a complex catalyst system and a base whose conjugate acid has a pKa in dimethyl sulfoxide (25° C., 1 bar) of at least 6.

The Phosphonic Acid Derivative

The phosphonic acid derivatives used in the process of the invention are generally known and have, for example, the formula (II)

where $R^5$ and $R^6$ are each, independently of one another, a carbon-comprising organic radical. For the definition of the term "carbon-comprising organic radical", reference is made to what has been said above in the definition of the radicals $R^1$ to $R^4$ in the formula (I).

$R^5$, $R^6$ are (independently of $R^{1-4}$) preferably radicals and groups as have also been defined above for $R^{1-2}$.

Phosphonic acid derivatives of the formula (II) are generally prepared by reacting phosphorus trichloride with the appropriate alcohols and/or the appropriate phenols.

Further details may be found, for example, in Ullmann's Encyclopedia of Industrial Chemistry, 6th edition, 1999 Electronic Release, Chapter "Phosphorus Compounds, Organic—Phosphites and Hydrogenphosphonates".

The process of the invention is preferably carried out using a phosphonic acid derivative (II) in which the radicals $R^5$ and $R^6$ are each, independently of one another, an unbranched or branched, acyclic or cyclic, unsubstituted or substituted alkyl radical which has from 1 to 20 aliphatic carbon atoms and in which one or more of the $CH_2$ groups may also be replaced by heteroatoms such as —O— or by heteroatom-comprising groups such as —CO— or —NR— and in which one or more of the hydrogen atoms may be replaced by substituents such as aryl (e.g. phenyl), alkyl (e.g. $C_{1-10}$-alkyl), hydroxyalkyl (e.g. $C_{1-10}$-hydroxyalkyl), haloalkyl (e.g. $C_{1-10}$-haloalkyl), acetoxyalkyl (e.g. acetoxy-$C_{1-10}$-alkyl);

an unsubstituted or substituted aromatic radical which has one ring or two or three fused rings and in which one or more ring atoms may be replaced by heteroatoms such as nitrogen and in which one or more of the hydrogen atoms may be replaced by substituents such as alkyl or aryl groups;

or in which the radicals $R^5$ together with $R^6$ form an unbranched or branched, acyclic or cyclic, unsubstituted or substituted $C_4$-$C_{20}$-alkylene radical which has from 4 to 10 atoms in the alkylene chain and in which $CH_2$ groups may also be replaced by heteroatoms such as —CO—, —O— or —NR— and in which one or more of the hydrogen atoms may be replaced by substituents such as aryl groups.

Examples of preferred radicals $R^5$ and $R^6$ are $C_1$-$C_{12}$-alkyl, particularly preferably methyl, ethyl, 1-propyl, 2-propyl, 1-butyl, 2-butyl, 2-methyl-1-propyl, 2-methyl-2-propyl, 1-pentyl, 1-hexyl, 1-octyl, 2-ethyl-1-hexyl, 1-decyl and 1-dodecyl;

$C_6$-$C_{10}$-aryl, particularly preferably phenyl;

$C_7$-$C_{10}$-aralkyl, particularly preferably phenylmethyl; and $C_7$-$C_{10}$-alkaryl, particularly preferably 2-methylphenyl, 3-methylphenyl and 4-methylphenyl.

In particular, the phosphonic acid derivative is a dialkyl or diaryl ester.

Very particular preference is given to using the dimethyl ester, the diethyl ester, the dipropyl ester, the dibutyl ester, the di-(2-ethylhexyl) ester or the diphenyl ester of phosphonic acid as phosphonic acid derivative in the process of the invention.

The Alkyne

The alkynes used in the process of the invention have the formula (III)

$$R^7-C\equiv C-R^8 \quad (III),$$

where $R^7$ and $R^8$ are each, independently of one another, hydrogen or a carbon-comprising organic radical. $R^7$ and $R^8$ can optionally also be joined to one another. For the definition of the term "carbon-comprising organic radical", reference is made to what has been said above in the definition of the radicals $R^1$ to $R^4$ in the formula (I).

$R^7$, $R^8$ are (independently of $R^{1-4}$) preferably radicals and groups as have also been defined above for $R^{1-2}$.

In the process of the invention, preference is given to using an alkyne (III) in which the radicals $R^7$ and $R^8$ are each, independently of one another, hydrogen (H);

or a substituted alkyl radical which has from 1 to 20 aliphatic carbon atoms and in which one or more of the $CH_2$ groups may also be replaced by heteroatoms such as —O— or by heteroatom-comprising groups such as —CO— or —NR— and in which one or more of the hydrogen atoms may be replaced by substituents such as aryl groups;

an unsubstituted or substituted aromatic radical which has one ring or two or three fused rings and in which one or more ring atoms may be replaced by heteroatoms such as nitrogen and in which one or more of the hydrogen atoms may be replaced by substituents such as alkyl or aryl groups.

Examples of preferred radicals $R^7$ and $R^8$ are hydrogen (H);

$C_1$-$C_{10}$-alkyl, particularly preferably methyl, ethyl, 1-propyl, 1-butyl, 1-pentyl and 1-hexyl;

$C_6$-$C_{10}$-aryl, particularly preferably phenyl;

$C_7$-$C_{10}$-aralkyl, particularly preferably phenylmethyl; and $C_7$-$C_{10}$-alkaryl, particularly preferably 2-methylphenyl, 3-methylphenyl and 4-methylphenyl.

Particular preference is given to using ethyne or propyne, very particularly preferably ethyne(acetylene), as alkyne in the process of the invention.

The Complex Catalyst System

The process is preferably performed in the presence of an Ni complex.

In particular, the complex catalyst system is an organophosphorus Ni complex.

It is in this case possible to use, in particular, organophosphorus complexes in which the nickel is divalent, Ni(II), or the nickel atom is present in the oxidation state zero [=Ni(0)].

Very particular preference is given to organophosphorus Ni(0) complexes.

Such organophosphorus Ni(0) complexes preferably comprise (a) nickel, (b) at least one phosphine having at least two trivalent phosphorus atoms and, if appropriate, additionally (c) at least one phosphine having one trivalent phosphorus atom.

Phosphine (b)

Phosphines having one trivalent phosphorus atom are generally referred to as monophosphines, phosphines having two trivalent phosphorus atoms are generally referred to as diphosphines, phosphines having three trivalent phosphorus atoms are generally referred to as triphosphines, etc.

The complexes preferably comprise phosphines having two trivalent phosphorus atoms.

In general, the phosphines having at least two trivalent phosphorus atoms which are used in the process of the invention have the general formula (I)

where $R^1$, $R^2$, $R^3$ and $R^4$ are each, independently of one another, a carbon-comprising organic radical and X is a carbon-comprising organic bridging group.

For the purposes of the present invention, a carbon-comprising organic radical is an unsubstituted or substituted, aliphatic, aromatic or araliphatic radical having from 1 to 30 carbon atoms. This radical can comprise one or more heteroatoms such as oxygen, nitrogen, sulfur or phosphorus, for example —O—, —S—, —NR—, —CO—, —N=, —PR— and/or —$PR_2$, and/or be substituted by one or more functional groups comprising, for example, oxygen, nitrogen, sulfur and/or halogen, for example by fluorine, chlorine, bromine, iodine and/or a cyano group (the radical R is in this case likewise a carbon-comprising organic radical). If the carbon-comprising organic radical comprises one or more heteroatoms, it can also be bound via a heteroatom. Thus, for example, ether, thioether and tertiary amino groups are also included. The carbon-comprising organic radical can be a monovalent or polyvalent, for example divalent, radical.

For the purposes of the present invention, a carbon-comprising organic bridging group is a substituted or unsubstituted, aliphatic, aromatic or araliphatic divalent group having from 1 to 20 carbon atoms and from 1 to 10 atoms in the chain. The organic bridging group may comprise one or more heteroatoms such as oxygen, nitrogen, sulfur or phosphorus, for example —O—, —S—, —NR—, —CO—, —N=, —PR— and/or —$PR_2$, and/or be substituted by one or more functional groups comprising, for example, oxygen, nitrogen, sulfur and/or halogen, for example by fluorine, chlorine, bromine, iodine and/or a cyano group (the radical R is in this case likewise a carbon-comprising organic radical). If the organic bridging group comprises one or more heteroatoms, it can also be bound via a heteroatom. Thus, for example, ether, thioether and tertiary amino groups are also included.

The process of the invention is preferably carried out using a phosphine (I) in which the radicals $R^1$, $R^2$, $R^3$ and $R^4$ are each, independently of one another, an unbranched or branched, acyclic or cyclic, unsubstituted or substituted alkyl radical which has from 1 to 20 aliphatic carbon atoms and in which one or more of the $CH_2$ groups may also be replaced by heteroatoms such as —O— or by heteroatom-comprising groups such as —CO— or —NR— and in which one or more of the hydrogen atoms may be replaced by substituents such as aryl groups;

an unsubstituted or substituted aromatic radical which has one ring or two or three fused rings and in which one or more ring atoms may be replaced by heteroatoms such as nitrogen and in which one or more of the hydrogen atoms may be replaced by substituents such as alkyl or aryl groups;

or in which the radicals $R^1$ together with $R^2$ and/or $R^3$ together with $R^4$ form an unsubstituted or substituted, aliphatic, aromatic or araliphatic group having from 3 to 10 atoms in the chain.

Examples of preferred monovalent radicals $R^1$, $R^2$, $R^3$ and $R^4$ are methyl, ethyl, 1-propyl, 2-propyl(sec-propyl), 1-butyl, 2-butyl(sec-butyl), 2-methyl-1-propyl(isobutyl), 2-methyl-2-propyl(tert-butyl), 1-pentyl, 2-pentyl, 3-pentyl, 2-methyl-2-butyl(tert-amyl), 1-hexyl, 2-hexyl, 3-hexyl, 2-methyl-2-pentyl, 3-methyl-3-pentyl, 2-methoxy-2-propyl, methoxy, ethoxy, 1-propoxy, 2-propoxy(sec-propoxy), 1-butoxy, 2-butoxy(sec-butoxy), 2-methyl-1-propoxy(isobutoxy), 2-methyl-2-propoxy(tert-butoxy), 1-pentoxy, 2-pentoxy, 3-pentoxy, 2-methyl-2-butoxy(tert-amoxy), 1-hexoxy, 2-hexoxy, 3-hexoxy, 2-methyl-2-pentoxy, 3-methyl-3-pentoxy, phenyl, 2-methylphenyl(o-tolyl), 3-methylphenyl(m-tolyl), 4-methylphenyl(p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin)yl, 1-naphthyl, 2-naphthyl, 2-quinolyl, 8-quinolyl, 1-isoquinolyl and 8-isoquinolyl.

Examples of preferred divalent radicals $R^1$ together with $R^2$ and/or $R^3$ together with $R^4$ are 1,4-butylene, 1,4-dimethyl-1,4-butylene, 1,1,4,4-tetramethyl-1,4-butylene, 1,4-dimethoxy-1,4-butylene, 1,4-dimethyl-1,4-dimethoxy-1,4-butylene, 1,5-pentylene, 1,5-dimethyl-1,5-pentylene, 1,5-dimethoxy-1,5-pentylene, 1,1,5,5-tetramethyl-1,5-pentylene, 1,5-dimethyl-1,5-dimethoxy-1,5-pentylene, 3-oxa-1,5-pentylene, 3-oxa-1,5-dimethyl-1,5-pentylene, 3-oxa-1,5-dimethoxy-1,5-pentylene, 3-oxa-1,1,5,5-tetramethyl-1,5-pentylene, 3-oxa-1,5-dimethyl-1,5-dimethoxy-1,5-pentylene,

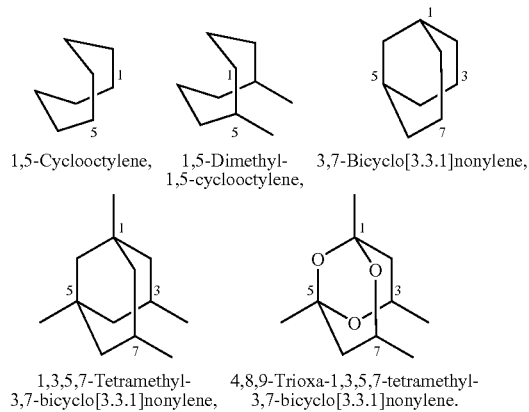

1,5-Cyclooctylene, 1,5-Dimethyl-1,5-cyclooctylene, 3,7-Bicyclo[3.3.1]nonylene, 1,3,5,7-Tetramethyl-3,7-bicyclo[3.3.1]nonylene, 4,8,9-Trioxa-1,3,5,7-tetramethyl-3,7-bicyclo[3.3.1]nonylene.

The process of the invention is particularly preferably carried out using a phosphine (I) in which $R^1$, $R^2$, $R^3$ and/or $R^4$ are each, independently of one another, an unsubstituted or substituted $C_3$-$C_{12}$-alkyl radical in which not more than one atom from the group consisting of hydrogen, fluorine, chlorine, bromine and iodine is bound to the α-carbon atom; and/or in which $R^1$, $R^2$, $R^3$ and/or $R^4$ are each, independently of one another, an unsubstituted or substituted aromatic radical which has 6 ring atoms and in which one, two or three ring atoms may be replaced by nitrogen; and/or in which $R^1$ together with $R^2$ and/or $R^3$ together with $R^4$ form an unsubstituted or substituted, aliphatic, aromatic or araliphatic group having from 4 to 7 atoms in the chain and a total of not more than 30 carbon atoms.

The unsubstituted or substituted $C_3$-$C_{12}$-alkyl radical in which not more than one atom from the group consisting of hydrogen, fluorine, chlorine, bromine and iodine is bound to the α-carbon atom is referred to as an alkyl radical branched at the α-carbon atom. Preference is given to at least two further carbon atoms being bound to the α-carbon atom. The third atom bound to the α-carbon atom is preferably hydrogen, carbon or a heteroatom such as oxygen, nitrogen or sulfur. Preferred examples are 2-propyl(sec-propyl), 2-butyl (sec-butyl), 2-methyl-2-propyl(tert-butyl), 2-methyl-2-butyl (tert-amyl) and 2-methoxy-2-propyl.

Preferred examples of an unsubstituted or substituted aromatic radical which has 6 ring atoms and in which one, two or three ring atoms may be replaced by nitrogen are phenyl, 2-methylphenyl(o-tolyl), 3-methylphenyl(m-tolyl), 4-methylphenyl(p-tolyl), 2,6-dimethylphenyl, 2,4-dimethylphenyl, 2,4,6-trimethylphenyl and 2-pyridyl.

Preferred examples of divalent radicals $R^1$ together with $R^2$ and/or $R^3$ together with $R^4$ are 1,1,4,4-tetramethyl-1,4-butylene, 1,4-dimethyl-1,4-dimethoxy-1,4-butylene, 1,1,5,5-tetramethyl-1,5-pentylene, 1,5-dimethyl-1,5-dimethoxy-1,5-pentylene, 1,5-dimethyl-1,5-cyclooctylene, 1,3,5,7-tetramethyl-3,7-bicyclo[3.3.1]nonylene and 4,8,9-trioxa-1,3,5,7-tetramethyl-3,7-bicyclo[3.3.1]nonylene.

The process of the invention is very particularly preferably carried out using a phosphine (I) in which the radicals $R^1$, $R^2$, $R^3$ and $R^4$ are each a 2-methyl-2-propyl(tert-butyl) or phenyl group.

The process of the invention is preferably carried out using a phosphine (I) in which X is an unsubstituted or substituted, aliphatic, aromatic or araliphatic group having from 1 to 8 atoms, preferably from 2 to 4 atoms, in the chain and a total of not more than 20 carbon atoms. In this group, one or more of the $CH_2$ groups may be replaced by heteroatoms such as —O— or by heteroatom-comprising groups such as —CO— or —NR— and/or one or more of the aromatic ring atoms may be replaced by heteroatoms such as nitrogen.

Examples of preferred bridging groups X are 1,2-ethylene, 1,3-propylene, 1,2-propylene, 1,4-butylene, 2-methyl-1,3-propylene, 1,5-pentylene, 2,2-dimethyl-1,3-propylene, 1,6-hexylene, —O—$CH_2CH_2$—O—, —O—$CH_2CH_2CH_2$—O—, o-phenylene, o-xylylene (=ortho-$CH_2$—$C_6H_4$—$CH_2$—) or 2,2'-biphenylene.

The process of the invention is particularly preferably carried out using a phosphine (I) in which the bridging group X is a 1,2-ethylene, 1,3-propylene, 1,4-butylene or o-xylylene group.

The process of the invention is very particularly preferably carried out using a phosphine (I) in which the radicals $R^1$ to $R^4$ are each a 2-methyl-2-propyl(tert-butyl) or phenyl group and X is a 1,2-ethylene, 1,3-propylene, 1,4-butylene or o-xylylene group. Very particularly preferred examples are 1,2-bis(di-tert-butylphosphino)ethane, 1,2-bis(diphenylphosphino)ethane, 1,3-bis(di-tert-butylphosphino)propane, 1,3-bis(diphenylphosphino)propane, 1,4-bis(di-tert-butylphosphino)butane, 1,4-bis(diphenylphosphino)butane, bis(di-tert-butylphosphino)-o-xylene and bis(diphenylphosphino)-o-xylene, in particular 1,3-bis(di-tert-butylphosphino)propane and 1,3-bis(diphenylphosphino)propane.

The synthesis of diphosphines is generally known and is described, for example, in L. Brandsma et al., "Application of Transition Metal Catalysts in Organic Synthesis", Springer-Verlag, Berlin 1997, pages 6 to 9.

Phosphine (c)

In addition to the above phosphine (b) having at least two trivalent phosphorus atoms, the complex can, if appropriate, additionally comprise at least one phosphine having one trivalent phosphorus atom (c). In a particular embodiment, the complex comprises both phosphine (b) and phosphine (a).

In general, the additional phosphine having one trivalent phosphorus atom (c) in the Ni complex catalyst system is a phosphine of the general formula (IV)

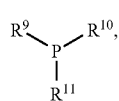

(IV)

where $R^9$, $R^{10}$, $R^{11}$ are each, independently of one another, a carbon-comprising organic radical.

For the purposes of the present invention, a carbon-comprising organic radical is an unsubstituted or substituted, aliphatic, aromatic or araliphatic radical having from 1 to 30 carbon atoms. This radical can comprise one or more heteroatoms such as oxygen, nitrogen, sulfur or phosphorus, for example —O—, —S—, —NR—, —CO—, —N=, —PR— and/or —PR$_2$, and/or be substituted by one or more functional groups comprising, for example, oxygen, nitrogen, sulfur and/or halogen, for example by fluorine, chlorine, bromine, iodine and/or a cyano group (the radical R is in this case likewise a carbon-comprising organic radical). If the carbon-comprising organic radical comprises one or more heteroatoms, it can also be bound via a heteroatom. Thus, for example, ether, thioether and tertiary amino groups are also included. The carbon-comprising organic radical can be a monovalent or polyvalent, for example divalent, radical.

$R^9$, $R^{10}$, $R^{11}$ are (independently of $R^{1-4}$) preferably radicals and groups as have also been defined above for $R^{1-4}$.

Very particular preference is given to $R^9$, $R^{10}$, $R^{11}$ each being a $C_{3-6}$-cycloaliphatic and/or aromatic radical such as cyclohexyl or phenyl.

In a preferred embodiment, the phosphine (c) having one trivalent phosphorus atom and the general formula (IV) in the Ni complex catalyst system is triphenylphosphine and/or tricyclohexylphosphine.

Preparation of the Complex

In the process of the invention, the complex catalyst system is generally prepared by combining an Ni(0) complex and the desired phosphines (b, or b and c) or by combining an Ni(II) compound, a reducing agent and the desired phosphines (b, or b and c).

Since the respective phosphonic acid derivative can also act as reducing agent, the complex catalyst system can also be obtained by combining an Ni(II) compound and the phosphines without a further reducing agent.

Ni(0) complexes suitable for carrying out the first variant are in principle all Ni complexes which react with the phosphine under the reaction conditions to form the complex catalyst system. Examples of suitable Ni complexes are tetracarbonylnickel, bis(cycloocta-1,5-diene)nickel and (cyclododeca-1,5,9-triene)nickel.

The Ni(II) compounds required for the second variant can be inorganic or organic in nature or have a mixed nature. Examples are nickel(II) halides (e.g. NiCl$_2$), nickel(II) sulfate, nickel(II) acetylacetonate, 1,3-bis(diphenylphosphino) propanenickel(II) chloride, hexaminenickel(II) chloride, nickel(II) bromide.diethylene glycol dimethyl ether complexes, dimethylnickel(II) complexes $(CH_3)_2NiL_2$ (L=e.g. triphenylphosphine, triethylphosphine, tributylphosphine) and dimethylnickel(II) complexes $(CH_3)_2NiL$ (L=e.g. tetramethylethylenediamine (TMEDA), bis(diphenylphosphino)propane, bis(diphenylphosphino)butane). Suitable reducing agents are, for example, elemental zinc, trialkylboron compounds, trialkylaluminum compounds, diisobutylaluminum hydride and phosphonic acid derivatives.

The complex catalyst system can be prepared in a separate step prior to the actual alkenylation of the phosphonic acid derivative or be prepared in-situ by combining the components mentioned.

The temperature in the preparation of the complex catalyst system is generally from 30 to 120° C., preferably from 60 to 110° C.

As solvent, it is generally possible to use the phosphonic acid derivative if this is liquid under the reaction conditions. However, it is also possible and may be advantageous to prepare the complex catalyst system in the presence of a further, inert solvent. In this case, preference is given to using the same solvents which can also be used as solvents for the alkenylation reaction and are described further below.

In general, a molar ratio of the phosphines (in the case of a plurality of phosphines, the molar total) to the nickel of the complex catalyst systems of from 0.5 to 6, preferably from 1 to 4 and particularly preferably from 1.5 to 2.5, is used in the process of the invention.

In the case of complexes comprising both phosphines (b) and phosphines (c), the molar ratio of nickel:(phosphine having at least two trivalent phosphorus atoms):(phosphine having one trivalent phosphorus atom) is preferably 1:(0.5-2):(1-4), in particular 1:(1-1.3):(1.5-2).

The molar ratio of the nickel of the complex catalyst system to the phosphorus of the phosphonic acid derivative and the products formed therefrom is generally from 0.01 to 10%, preferably from 0.05 to 5% and particularly preferably from 0.05 to 3%, in the process of the invention.

The Base

The process of the invention is carried out in the presence of a base whose conjugate acid has a pKa of at least 6. The pKa indicates the strength of an acid and is the negative logarithm to the base ten of the acidity constant.

The pKa indicates the strength of an acid and is measured in dimethyl sulfoxide at 25° C., 1 bar.

The conjugate acid preferably has a pKa of from 6 to 20, very particularly preferably from 6 to 16 and in particular from 6 to 14. In a particular embodiment, the lower limit is at least 8, and the preferred ranges are correspondingly from 8 to 20, from 8 to 16 and from 8 to 14.

In a very particularly preferred embodiment, the pKa is from 11.5 to 12.5.

The base is preferably an organic nitrogen compound.

The base is generally a low molecular weight compound having a molecular weight of less than 1000 g/mol, in particular less than 500 g/mol.

Preferred bases are, in particular, diazo compounds.

Particular preference is given to 1,8-diazabicyclo[5.4.0] undec-7-ene (DBU).

The base is preferably used in amounts of from 0.1 to 5 mol %, particularly preferably in amounts of from 0.2 to 3 mol % and very particularly preferably in amounts of from 0.5 to 2 mol %, based on the phosphonic acid derivative.

The Reaction

The process of the invention can, in particular, be carried out at a temperature of from 0 to 200° C., preferably from 20 to 150° C., particularly preferably from 50 to 120° C., in particular from 50 to 100° C.

It is generally carried out at a pressure of from 0.01 to 5 MPa abs., preferably from 0.05 to 2.5 MPa abs., particularly preferably from 0.05 to 0.14 MPa abs., in particular at atmospheric pressure.

The process of the invention can be carried out in the absence of an additional solvent ("solvent-free") or in the presence of an inert solvent. For the purposes of the present invention, inert solvents are solvents which do not react chemically with the compounds used under the reaction conditions set. Suitable inert solvents are, for example, tetrahydrofuran, 1,4-dioxane, N-methylpyrrolidone, N-methylpiperidone, dimethyl sulfoxide, toluene, xylene, glycol ethers (e.g. 1,2-dimethoxyethane(ethylene glycol dimethyl ether), bis(2-methoxyethyl) ether(diethylene glycol dimethyl ether), triethylene glycol dimethyl ether or tetraethylene glycol dimethyl ether), dimethylformamide, dimethylformanilide, chlorobenzene and mixtures thereof. The addition of an inert solvent can be advantageous, for example, when using relatively high molecular weight, viscous or solid (under the reaction conditions) phosphonic acid derivatives.

It may be advantageous to carry out the process of the invention in the presence of a free-radical inhibitor as additive. Free-radical inhibitors which are suitable in principle are the inhibitors which are generally customary in industry, for example N,N'-bis(1-methylpropyl)-1,4-phenylenediamine, 2,6-di-tert-butyl-4-methylphenol or 1,2-dihydroxybenzene (catechol). If a free-radical inhibitor is used, a molar ratio of the free-radical inhibitor to the phosphorus of the phosphonic acid derivative and the products formed therefrom of from 0.01 to 10%, preferably from 0.05 to 5% and particularly preferably from 0.5 to 3%, is generally set.

The process of the invention is very particularly preferably used to prepare dimethyl ethenylphosphonate, diethyl ethenylphosphonate, di-n-propyl ethenylphosphonate and di-n-butyl ethenylphosphonate.

When, for example, phenylacetylene or, for example, 1-octyne and dimethyl phosphite are used, three isomeric alkenylphosphonic diesters can be formed as reaction products according to the following reaction equation (R'=phenyl or R'=n-hexyl):

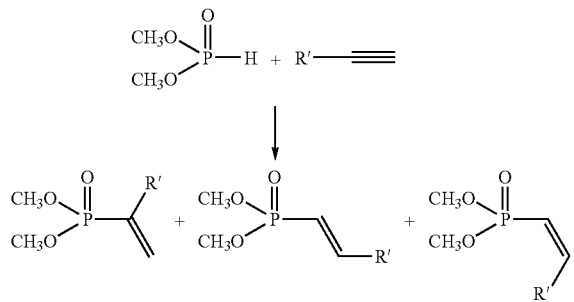

The process of the invention can be carried out batchwise, semicontinuously or continuously.

In an illustrative embodiment of a batch process, the phosphines (e.g. the two phosphines (b, c), in particular the two phosphines of the formulae I and IV), the Ni(0) complex (or the Ni(II) compound and the reducing agent), the phosphonic acid derivative, the base, if appropriate a solvent and if appropriate a free-radical inhibitor are combined, mixed and brought to the reaction conditions. After a short time, generally after from 1 to 60 minutes, preferably from 5 to 30 minutes, the alkyne is added to the reaction mixture which has been brought to the reaction conditions. After the reaction is complete, the reaction mixture is passed to work-up, preferably by distillation, and the desired alkenylphosphonic acid derivative is isolated.

In an illustrative embodiment of a semicontinuous process, the phosphines (e.g. the two phosphines (b, c), in particular the two phosphines of the formulae I and IV), the Ni(0) complex (or the Ni(II) compound and the reducing agent), the phosphonic acid derivative, the base, if appropriate a solvent and if appropriate a free-radical inhibitor are combined, mixed and brought to the reaction temperature. The alkyne is then, preferably after the reaction mixture has been maintained at the reaction temperature for a short time, generally from 1 to 60 minutes, preferably from 5 to 30 minutes, introduced continuously until the desired amount has been reached. It is advantageous to add the alkyne after the two phosphines (b, c), the Ni complex (or the Ni(II) compound and the reducing agent) and the phosphonic acid derivative have been combined, mixed and brought to the reaction conditions. The alkyne can be introduced in gaseous or liquid form. When it is added in liquid form, it is possible to use pure, liquid alkyne or a solution in a solvent. After the introduction of alkyne is complete, the reaction mixture can be left for a further time under the reaction conditions. After the reaction is complete, the reaction mixture is passed to work-up, preferably by distillation, and the desired alkenylphosphonic acid derivative is isolated.

In an illustrative embodiment of a continuous process, the phosphines (e.g. the two phosphines (b, c), in particular the two phosphines of the formulae I and IV), the Ni complex (or the Ni(II) compound and the reducing agent), the base, if appropriate a solvent and if appropriate a free-radical initiator are combined, mixed and brought to the reaction temperature. The phosphonic acid derivative and the alkyne are then introduced continuously in the desired ratio. In general, the phosphonic acid derivative is added in liquid form, if appropriate as a solution in a solvent. It can be introduced in gaseous or liquid form. When it is added in liquid form, it is possible to use pure, liquid alkyne or a solution in a solvent. Liquid reaction mixture is removed continuously and the alkenylphosphonic acid derivative formed is isolated in a subsequent stage, for example by distillation or extraction. If appropriate, relatively high-boiling by-products are also separated off. The remaining mixture, which comprises mainly unreacted phosphonic acid derivative and any solvent used can, if appropriate, be recirculated.

The process of the invention makes it possible to prepare alkenylphosphonic acid derivatives at a reaction temperature of preferably below 150° C. without use of an expensive noble metal catalyst in only one synthesis step starting from readily available starting compounds. Since the reaction is a very selective addition reaction, no coproducts and only a small amount of by-products are formed. The process of the invention allows a high yield of significantly above 50%, in particular above 75%, to be obtained with good process economics at catalyst costs below those in EP-A1-1 203 773. Very high yields and selectivities are also achieved without purification or distillation of the starting compounds, in particular the phosphonic acid derivative.

The vinylphosphonic acid can easily be prepared by hydrolysis of the alkenylphosphonic acid derivatives obtained.

The alkenylphosphonic acid derivatives obtained or the vinylphosphonic acids prepared therefrom are suitable as monomers for the preparation of polymers which are suitable for a variety of uses. Such polymers are particularly useful as binders for paints, varnishes or other protective coatings, in particular for corrosion protection.

EXAMPLE

In a three-neck flask provided with internal thermometer, condenser and gas inlet tube, 50 g of technical-grade dimethyl phosphite (DMP) were admixed with 0.3 mol % (based on DMP) of nickel acetate tetrahydrate, 0.6 mol % of dppp (dppp=1,3-bis(diphenylphosphino)propane) and 1 mol % of DBU and the reaction solution was heated to 95° C. and stirred at this temperature for 10 minutes. 8 l/h of acetylene were then passed into the reaction solution at 100° C. and atmospheric pressure for 1.5 hours. After work-up by distillation, dimethyl vinylphosphonate (DMVP) was isolated in a yield of 87%.

The yield in the hydrophosphonylation of acetylene by means of technical-grade dimethyl phosphite was determined with addition of various bases. The evaluation and determination of the proportions by weight in the reaction mixture were carried out by means of gas chromatography using NMP as internal standard. All bases were used in an amount of 1 mol % based on dimethyl phosphite.

| No. | Yield [%] | Base | pKa of the conjugate acid |
|---|---|---|---|
| 1 | 87 | 1,8-Diazabicyclo[5.4.0]undec-7-ene (DBU) | 12 |
| 2 | 78 | Methylimidazole | 7.2 |
| 3 | 55 | 1,4-Diazabicyclo[2.2.2]octane | 8.93 |
| 4 | 49 | Imidazole | 6.95 |
| 5 | 47 | Pyridine-2-carboxyaldehyde | 6.5 |
| 6 | 39 | Benzylamine | 9.36 |
| 7 | 35 | Piperidine | 11.12 |
| 8 | 22 | No additive | — |
| 9 | 21 | Aniline | 3.6 |
| 10 | 14 | Pyrazole | 2.5 |
| 11 | 9 | Pyrrole | −9 |
| 12 | 6 | Tetrazole as acetonitrile solution | 4.9 |
| 13 | 1 | Pyridine | 5.06 |

The invention claimed is:

1. A process for preparing an alkenylphosphonic acid derivative, comprising reacting a phosphonic acid derivative with an alkyne in the presence of a complex catalyst system and a base whose conjugate acid has a pKa in dimethyl sulfoxide (25° C., 1 bar) of at least 6,
wherein the complex catalyst system is an organophosphorus Ni(0) complex.

2. The process according to claim 1, wherein the phosphonic acid derivative is a dialkyl or diaryl ester.

3. The process according to claim 1, wherein the phosphonic acid derivative is the dimethyl ester, the diethyl ester, the dipropyl ester, the dibutyl ester, the di(2-ethylhexyl)ester or the diphenyl ester of phosphonic acid.

4. The process according to claim 1, wherein the alkyne is ethyne (acetylene) or propyne.

5. The process according to claim 1, wherein the complex catalyst system comprises
(a) nickel(0),
(b) at least one phosphine having at least two trivalent phosphorus atoms and, optionally
(c) at least one phosphine having one trivalent phosphorus atom.

6. The process according to claim 1, wherein the complex catalyst system is prepared by combining an Ni(0) complex and a phosphine or by combining an Ni(II) compound, a reducing agent and a phosphine.

7. The process according to claim 1, wherein from 0.01 to 10 mol % of nickel of the complex catalyst system, based on the phosphonic acid derivative to be reacted, is used.

8. The process according to claim 1, wherein the conjugate acid of the base used has a pKa of from 6 to 14.

9. The process according to claim 1, wherein the base is an organic nitrogen compound.

10. The process according to claim 1, wherein the base is an azo compound.

11. The process according to claim 1, wherein the base is 1,8-diazabicyclo[5.4.0]undec-7-ene (DBU).

12. The process according to claim 1, wherein the base is used in amounts of from 0.05 to 5 mol %, based on the phosphonic acid derivative.

13. The process according to claim 1, wherein the reaction is carried out at a temperature of from 20 to 150° C. and a pressure of from 0.05 to 2.5 MPa abs.

14. The process according to claim 1 for preparing a dialkyl vinylphosphonate by reacting a corresponding dialkyl phosphonate with acetylene.

15. The process according to claim 1, wherein the yield of the alkenylphosphonic acid derivative is above 50%.

16. The process according to claim 1, wherein the yield of the alkenylphosphonic acid derivative is above 75%.

* * * * *